United States Patent
Meruelo et al.

(10) Patent No.: US 6,503,499 B1
(45) Date of Patent: *Jan. 7, 2003

(54) VIRAL VECTOR COMPLEXES HAVING ADAPTERS OF PREDEFINED VALENCE

(75) Inventors: Daniel Meruelo, Scarborough, NY (US); Koichi Ono, New York, NY (US); Christine Pampeno, New York, NY (US)

(73) Assignee: New York University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/079,882

(22) Filed: May 15, 1998

Related U.S. Application Data

(63) Continuation of application No. 08/363,137, filed on Dec. 23, 1994, now Pat. No. 5,753,499.

(51) Int. Cl.[7] .................. A61K 48/00; C12N 15/74; C12N 5/00
(52) U.S. Cl. ............... 424/93.2; 435/320.1; 435/235; 435/456; 514/44
(58) Field of Search .................. 514/44; 435/320.1, 435/235, 455, 456; 424/93.2

(56) References Cited

U.S. PATENT DOCUMENTS

| | | | |
|---|---|---|---|
| 5,328,985 A | | 7/1994 | Sano et al. .................. 530/350 |
| 5,753,499 A | * | 5/1998 | Meruelo et al. .......... 435/320.1 |

OTHER PUBLICATIONS

Microbiology by Prescott et al. pp. 307–325, 1990. Wm.C. Brown Publishers.*
Roux et al., Proc. Natl. Acad. Sci. USA, 86:9079–9083 (1989).
Sano et al., Bio/Technology, 9:1378–1381 (1991).
Etienne—Julan et al., Bone Marrow Transplantation, 9 (Suppl. 1):139–142, 1992.
Etienne—Julan et al., J. General Virology, 73:3251–3255 (1992).
Roux et al., Vectors as Tools for the Study of Normal and Abnormal Growth and Differentiation, H34:153–164 (1989).
Etienne—Julan et al., Human Gene Transfer, 219:177–184 (1991).

* cited by examiner

Primary Examiner—Ram R. Shukla
(74) Attorney, Agent, or Firm—Darby & Darby

(57) ABSTRACT

The invention concerns an improvement in the art of inserting and expressing foreign gene into eukaryotic cells. The invention particularly concerns methods and compositions whereby viral vectors can be used to insert and express foreign genes into specifically cells having particular differentiation antigens. A method of determining which differentiation antigens can be used is taught. The invention encompasses complexes of viral particles and adapters that cause the binding and internalization of the vector particles such that a gene of interest in the particle is expressed.

10 Claims, 5 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 1:

GGACTAGTTC CGAATCGTGG TCTCGCTGA 29

(2) INFORMATION FOR SEQ ID NO: 2:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 2:

GGGAATTCCA TATGGGGGTT GACCCCTCCG AG 32

(2) INFORMATION FOR SEQ ID NO: 3:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 3:

AATTCGGGAG GCGGTGGATC AGGTGGAGGC GGTTCAGG 38

(2) INFORMATION FOR SEQ ID NO: 4:

(i) SEQUENCE CHARACTERISTICS:
(A) LENGTH: 38 base pairs

-continued

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GATCCCTGAA CCGCCTCCAC CTGATCCACC GCCTCCCG                              38
```

VIRAL VECTOR COMPLEXES HAVING ADAPTERS OF PREDEFINED VALENCE

CROSS-REFERENCE TO RELATED APPLICATION

Figure 1:
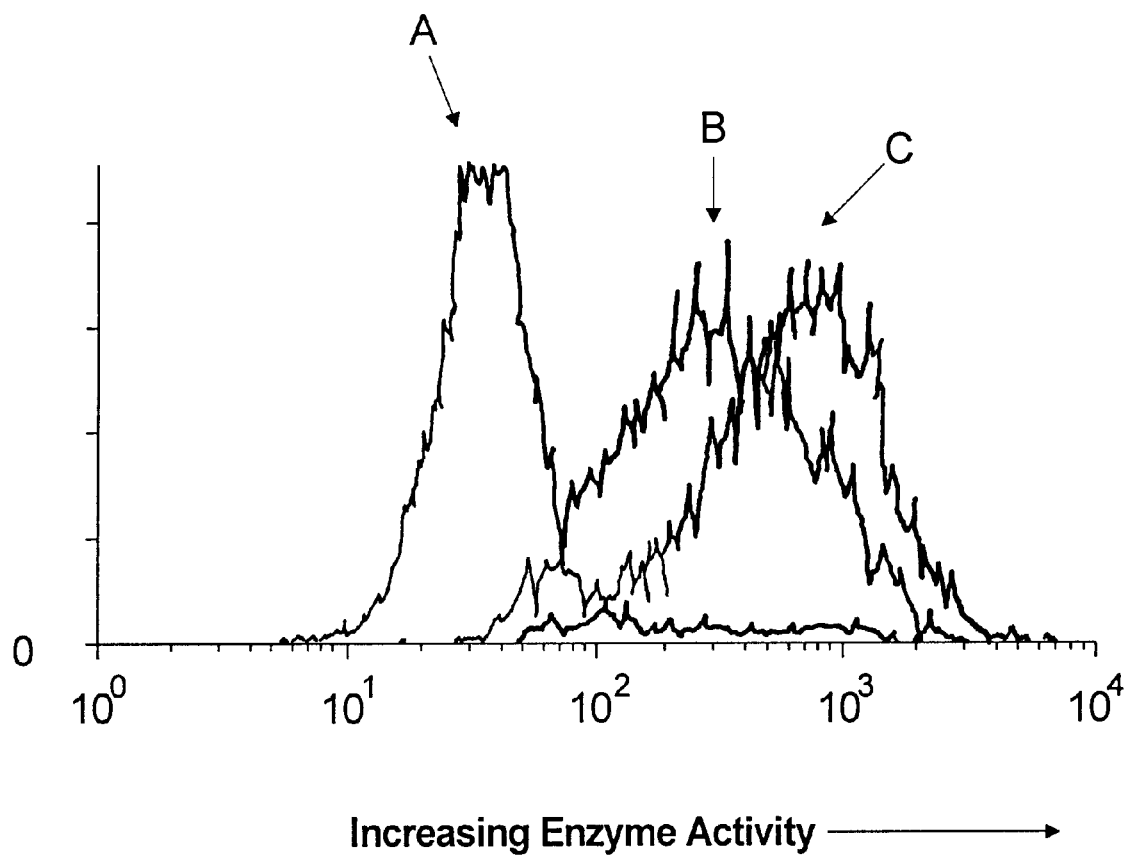

This application is a continuation of U.S. Ser. No. 08/363,137, filed Dec. 23, 1994 now U.S. Pat. No. 5,753,499, the contents of which are incorporated in its entirety by reference herein.

1. FIELD OF THE INVENTION

The invention involves viral vectors that can be used to transduce a target cell, i.e., to introduce genetic material into the cell. The targets of interest are eukaryotic cells and particularly human cells. The transduction can be done in vivo or in vitro. More particularly the invention concerns viral vectors, that can be used to transduce one from among many types of cell that has a particular acceptor molecule exposed on the target cell's surface.

2. BACKGROUND OF THE INVENTION

A variety of viral based vectors have been employed to transfer and to express a gene of interest into a eukaryotic target cell. Recombinant DNA techniques are used to replace one or more of the genes of the virus with the gene of interest operably linked to a promoter that is functional in the target cell. The construct, termed a viral vector, infects the target cell, using the physiological infective "machinery" of the virus, and expresses the gene of interest instead of the viral genes. Because not all the genes of the virus are present in the vector, infection of the target by the vector does not produce viral particles. Viruses that have been used to infect human or mammalian target cells include herpes virus, adenovirus, adeno associated virus and derivatives of leukemia-type retroviruses. Among the retroviruses of particular interest in the transduction of cells of human origin are constructs based on amphotropic retroviruses.

2.1. Use of Amphotropic Retrovirus Vectors

Retroviruses are particularly well suited for transduction of eukaryotic cells. The advantages of a vector based this type of virus include its integration into the genome of the target cell so that the progeny of the transduced cell express the gene of interest. Secondly, there are well developed techniques to produce a stock of infectious vector particles that do not cause the production of viral particles in the transduced target cell. Lastly, the production and purification of stocks vector particles having titers of $10^6$ TCIU/ml can be accomplished.

One disadvantage of the use of retroviral vectors is that there is presently no practical general, method whereby a particular tissue or cell type of interest can be specifically transduced. Previous efforts to this end have included surgical procedures to limit to specific organs the physical distribution of the viral vector particles. Ferry, N., et al., 1991, Proc.Natl.Acad.Sci. 88:8377.

Alternatively, practitioners have taken advantage of the fact that type C retroviruses only infect dividing cells. Thus, a population of cells, e.g., bone marrow cells, was removed from a subject and cultured ex vivo in the presence of growth factors specific for the specific target cell which, thus, comprises most of dividing cells in the culture. See, e.g., Wilson, J. M., et al., 1990, Proc.Natl.Acad.Sci. 87:439–47; Ohashi, T., et al., 1992, Proc.Natl.Acad.Sci. 89:11332–36. After transduction the dividing cells must be harvested and, for many purposes, reimplanted into the subject. The technical difficulties of the ex vivo culture technique combined with the unavailability of growth factors of specific for some types of cells have limited the application of this approach.

A second difficulty presented by the use retroviral based vectors is that a retroviral particle contains two copies of its genome. There is a nonzero possibility of a genetic recombination between the alleles of the viral particles. Such recombination can give rise to a replication competent virus that can cause the production of infectious particles by the target cell. In contrast to herpes virus or adenovirus infection retroviral infections are not necessarily self-limiting.

Notwithstanding these difficulties retrovirus vectors, based on amphotropic murine leukemia retroviruses that infect human cells, have been approved for use in human gene therapy of certain diseases, for example adenosine deaminase and low density lipoprotein receptor deficiencies and Gaucher's Disease. See, e.g., Miller A. D., 1992, Nature 357:455; Anderson, W. F., 1992, Science 256:808.

One approach to overcoming the limitations of using amphotropic retrovirus vectors in human cells has been to mutate the gene encoding the protein on the viral surface that determines the specificity of infection of the virus, the gp70 protein. Using recombinant DNA technology a "mutant" virus is constructed that has had small regions of the gp70 sequence replaced by predetermined sequences. The limits of this approach are set by the requirement for knowledge of the sequence that will enable infection of the target of interest. However, when this knowledge was available, the anticipated alteration in viral specificity has been observed. Valsesia-Wittmann, S., 1994, J.Virol. 68:4609–19.

2.2. The Use of Viral Vector Complexes to Transduce Target Cells

An alternative to altering the specificity of binding of the gp70 protein itself is to employ a second, novel structure that binds or is bonded to both the viral particle and to the target cell. Such novel, independently functioning molecules can be thought of as molecular adapters which, together with the viral particle form a vector complex. In one example of this approach, lactose molecules were covalently coupled, by a non-specific reaction, to the envelope proteins of an ecotropic retrovirus, which does not normally infect human cells. A human hepatocellular carcinoma that was known to have receptors for lactose-containing proteins was found to be susceptible to transduction by this vector complex, although the integration of the transduced gene of interest in the target cell chromosome was not directly demonstrated. Neda, H., et al., 1991, J.Biol.Chem. 266:14143. No evidence of expression was observed in a hepatocellular carcinoma that lacked the lactose specific receptor. The method of Neda results in a variable number of binding sites for the exposed acceptor on the target cell, attached to each derivatized or bound envelope protein and, of course, is limited to the case wherein the target cell has a lactose receptor.

Another approach to the use of adapter molecules involved an adapter that was not covalently coupled to the vector. The use of this type of adapter has been attempted by Roux and his colleagues, who have published several reports that relate to this strategy. Patent Publication FR 2,649,119 to Piecheczyk, Jan. 4, 1991; Roux P., et al., 1989, Proc. Natl. Acad. Sci. 86:9079–83; Etienne-Julan, M., et al., 1992, J. Gen. Virol. 73:3251–55. Roux and colleagues have constructed adapters from two types of proteins, both typically antibodies, by biotinylating the proteins and utilizing avidin or streptavidin tetramer, a protein which binds four biotin molecules, to form aggregates of up to four of the biotinylated proteins. The first type of proteins was an anti-gp70 antibody, which binds to the viral particle. The second type of protein was one of a variety of proteins that specifically bind to the target cells and could be an antibody or other protein. The adapter of Roux contained a streptavidin tetramer and four other protein molecules. Each adapter contained one streptavidin tetramer, but the aggregates were otherwise random, i.e., all possible combinations of the two other types of proteins were possible including aggregates having only anti-gp70 and only the target cell specific protein.

To offset the difficulties attendant with the use of mixtures of randomly aggregated proteins, Roux did not employ pre-formed adapters but rather constructed the adapters, in situ, i.e., on the surface of the target cell, by successively exposing the cells to the target cell specific protein, the streptavidin, the anti-gp70 and lastly to the viral vector itself. Even when constructed in situ, the adapter molecules of Roux consisted of a random mixture having no predetermined number of viral or target cell binding sites.

To allow for the completion of this multistep process the target cells must be prevented, by some means, from internalizing the components of the aggregates prior to their completion. The method adopted by Roux was to reduce the temperature of the culture. Thus, the work of Roux does not yield a system that can be used at all in an in vivo setting. Even ex vivo, the complex of adapter and vector must be constructed in a multistep process during which the metabolism of the target cell must be inhibited.

3. SUMMARY OF THE INVENTION

The invention concerns the use of viral vectors that have proteins on the surface of the viral particles, hereinafter termed envelope proteins, that do not bind to the target cell of interest. The invention involves a new type of adapter that provides a fixed, predefined valence, i.e., number of binding sites, specific for an exposed acceptor molecule on the target cell, on each envelope protein molecule having such an adapter. Because the binding sites for the viral particle and the target cell are different, the adapters of the invention can be constructed in the absence of the target cell. The preformed complexes of adapters and viral particles that can then be used to transduce a gene of interest into the target cell.

In one embodiment, the invention comprises a complex of a viral vector and a non-covalently bonded difunctional molecule, i.e, a molecule having at least one site for linking with the virus and a predefined number of binding sites specific for the target cell of interest. In a particular embodiment of this type, the difunctional molecule has a single binding site for the virus and a single site for the target cell.

The invention also encompasses complexes comprising a viral vector in which some or all of the envelope protein molecules of the virus are modified by formation a new covalent bond. There are three different embodiments of this form of the invention.

Firstly, the adapter molecule can be a binding polypeptide that replaces at least about 25 amino acids of the envelope protein of the virus and which, thereby, forms a fusion protein. Such fusion proteins can be made by linking, through recombinant DNA techniques, the fragment of the gene encoding the fragment of the envelope protein to a fragment of a gene that encodes a parent protein having the same, desired binding specificity as the binding polypeptide.

As used herein, a fusion protein is a protein having at least two blocks of contiguous sequence, of about 10 or more amino acids in length, that are derived from two different parent proteins. In a preferred embodiment, the viral particle contains a mixture of normal envelope proteins and fusion proteins.

Secondly the adapter can consist of a linking molecule and a polypeptide of an envelope protein/polypeptide fusion protein, as described above. The non-envelope polypeptide of the fusion protein is complementary to the linking molecule and is, hence, termed a linking polypeptide. In this embodiment, the linking molecule is not covalently bonded to the vector. Rather, the linking molecule is itself difunctional. It contains a ligand functionality, which is complementary to the linking polypeptide, affixed to the viral surface, and an acceptor binding portion which contains a predefined number of binding sites for an exposed acceptor on the target cell surface.

The third embodiment employs the linking molecule, as described above, but does not utilize an envelope protein/ linking polypeptide fusion protein. Rather in this embodiment a linking site is covalently affixed to the envelope protein after the vector particle has been constructed.

The invention further provides methods whereby a one skilled in the art can determine whether a particular antibody is suitable for use as a target cell specific protein and encompasses methods of use of the preformed viral vector complexes.

4. BRIEF DESCRIPTION OF THE FIGURES

FIG. 1. FACS histogram of β-galactosidase-dependent fluorescent staining of SupT1; A: untransduced; (B,C): transduced with a ψ-2BAG/SA-PA/anti-CD4 vector complex in two separate experiments.

Figure 2:
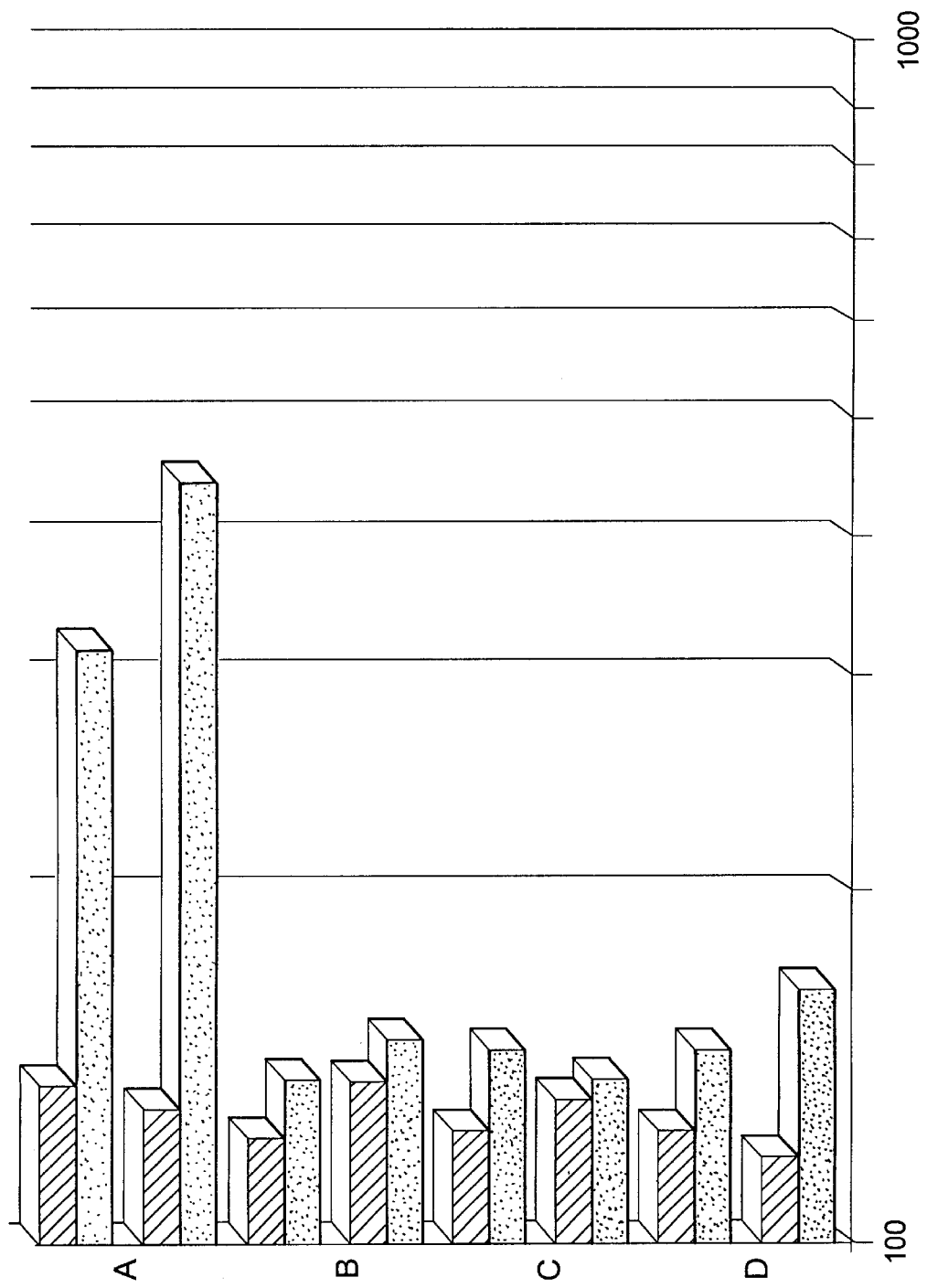
Figure 3:
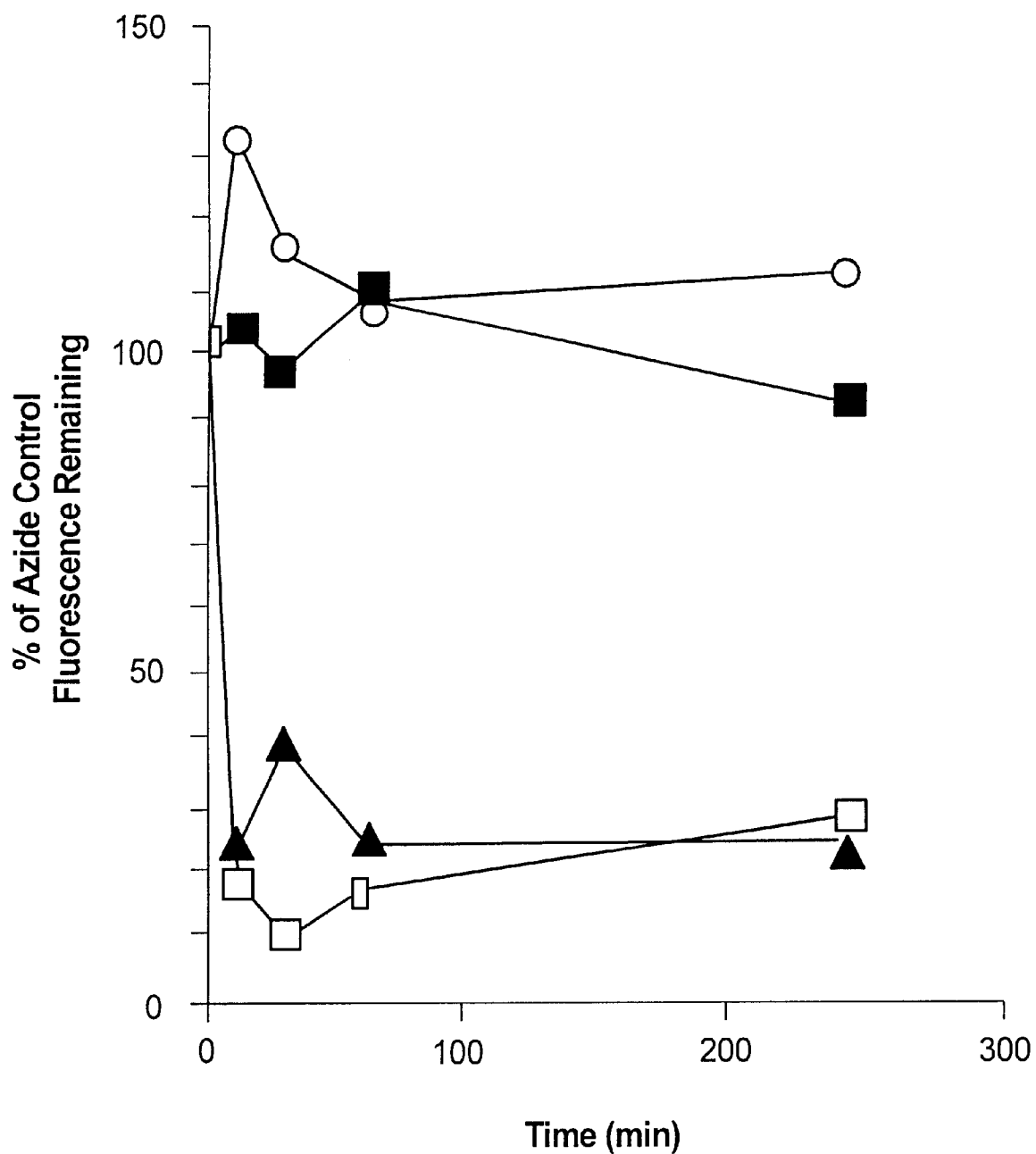
Figure 4:
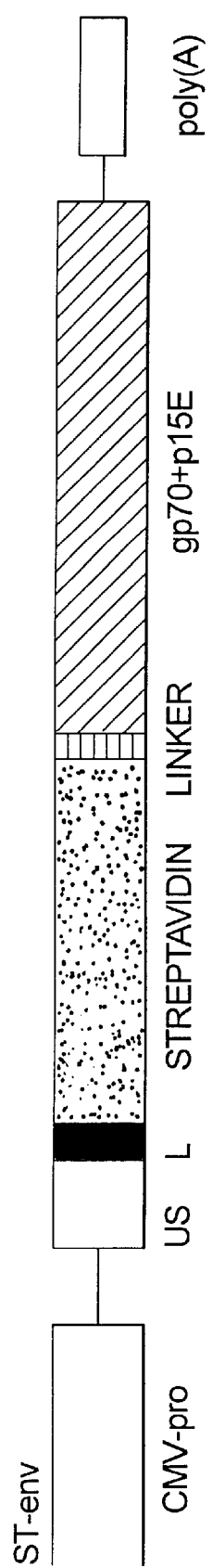

FIG. 2. Mean β-gal fluorescent staining of CD4$^+$ (stippled fill) and of B220$^+$ (diagonal fill) cells recovered from a transduced mouse in vivo: A: ψ-2BAG/SA-PA/anti-CD4 vector complex; B: ψ-2BAG/SA-PA only; C: ψ-2BAG; D: without viral particles. Results of two experimental animals are shown.

FIG. 3. Time course of the internalization of vector complexes. Daudi, anti-HLA-DR antibody only (-○-); SupT1, anti-CD4 antibody only (-■-); Daudi, vector complex (-▲-); SupT1, vector complex (-□-).

FIG. 4. Schematic of the gene encoding a streptavidin/env fusion protein and the operably linked cytomegalovirus promoter (CMV-pro) as found in pST-env.

FIGS. 5A and 5B. FACS histograms of β-gal fluorescent staining of transduced Daudi cells. FIG. 5A: ψ-2BAG (negative control). FIG. 5B: pST-env-ψ-2BAG/biotinylated anti-HLA-DR vector complex. Note the presence of cells in channels >100 in FIG. 5B only.

5. DETAILED DESCRIPTION OF THE INVENTION

The present invention provides for a means for modifying the genome of eukaryotic cells, such as mammalian cells or avian cells, and, more particularly, of human cells for medical practice and also of the cells of domesticated animals that are valuable for agriculture and recreational purposes for veterinary practice. The invention provides for the introduction and expression of genetic material into the cells by means of a viral vector complex. In the viral vector, some or all of the viral genes have been replaced by a gene that is to be expressed in the eukaryotic target cell. The essential viral genes that have been removed from the vector are, in general, inserted into the genome of the cell line that is used to produce stocks of the viral particles. The producer cells lines thus complement the defects that are present in the viral vector. In some embodiments, the only viral gene contained in the genome of the vector is a gene that is needed for the packaging of the vector genome into the viral particles.

The construction of viral-based vectors suitable for the general expression of genes in cells that are susceptible to infection by the virus is described the following patent publications: WO 89/05345 to Mulligan, R. C. and others, WO 92/07943 to Guild, B. C. and others concerning retroviral vectors; WO 90/09441 and WO 92/07945 to Geller, A. I. and others concerning herpes vectors; WO 94/08026 to Kahn, A. and others, and WO 94/10322 to Herz, J. and others concerning adeno virus vectors; and U.S. Pat. No. 5,354,678 to Lebkowski and U.S. Pat. No. 5,139,941 to Muzcyzka concerning adeno-associated virus. Packaging systems for the production of retroviral vectors have been described by Danos, O., and Mulligan, R. C., 1988, Proc. Natl.Acad.Sci. 85:6460–64, and by Landau, N. R., & Litmann, D. R., 1992, J.Virol. 66:5110–13.

The present invention is an improvement in the viral vector art. The invention replaces the viral vector with a vector complex which consists of two portions: a viral portion and a target cell specific portion termed an adapter. The adapter subserves the function of binding the vector to the target cell in such a way that the vector is internalized into the cell. This function is necessary for infection and expression of the gene of interest. Without limitation as to theory, the invention accomplishes two improvements by providing an adapter portion. Firstly, the use of an adapter allows the vector to be constructed so that it is unable to infect the target cell, or any cell from the same species, in the absence the adapter. In certain embodiments of the invention, the vector is based on a virus that is normally unable to infect the target species and the adapter is not encoded by a gene in the vector. Since infection is possible only when the adapter is present, a recombinant virus that causes an inadvertent, iatrogenic infection becomes virtually impossible.

Secondly, the adapter can be provided with a variety of specificities. The application discloses methods of constructing an adapter comprising an antibody specific for an acceptor on the target cell or an antigen binding fragment of the antibody, so long as the acceptor and attached vector complex are internalized into the target cell after the vector complex is bound. Thus, there are a large number of cell surface antigens suitable for use as acceptors and for which antibodies are already available. Such structures include, but are not limited to, the class I and class II Major Histocompatibility Antigens; receptors for a variety of cytokines and cell-type specific growth hormones, interleukins, interferons, fibroblast growth factors, erythropoietin, transforming growth factors, tumor necrosis factors, colony stimulating factors and epidermal growth factor; cell adhesion molecules; transport molecules for metabolites such as amino acids; the antigen receptors of B- and T-lymphocytes; and receptors for lipoproteins. The invention makes possible the specific infection of a cell type by allowing the employ of differentiation antigens as acceptors for the viral vector complex.

The invention is used to transduce a gene of interest into a target cell. In practicing the preferred embodiment of the invention, the complex of the viral vector and the adapter is formed prior to the interaction of the adaptor or of any part of the adaptor and the target cell acceptor.

The practice of the invention can be performed by culturing the target cells ex vivo. The cultured cells can be continued in culture to produce the product encoded by the transduced gene. Alternatively, the ex vivo transduced cell can be implanted into a subject, which can be the host from which the cultured cells were obtained.

In a yet further embodiment, the viral vector complex can be administered directly to the subject thereby obviating the need for any ex vivo cell culture. The routes of administration to the subject can be any route that results in contact between the vector complex and the target cell. Thus for example, intravenous administration is suitable for target cells in the hepatic, splenic, renal cardiac and circulatory or hematopoietic systems. The vector complex can also be administered by catheterization of the artery or vein leading to the target organ, thereby allowing the localized administration of the complex. The complex can also be administered by inspiration when the target cells are in the respiratory system.

Genes that can be transduced by the practice of the invention include any gene that can be expressed in a eukaryotic system. Illustrative examples of genes that can be expressed by use of the present invention include glucocerebrosidase, adenosine deaminase, and blood coagulation factors such as factor VIII and factor IX.

The viral component of the vector complex can be based on any virus, the particles of which are unable to bind or have been modified to be unable to bind to cells of the same species as the target cell. A non-limiting example of the first type of virus are the murine ecotropic leukemia retrovirus viruses, e.g., Moloney Leukemia Virus or AKV. Alternatively, chemically modified viral particles can be employed. By way of a non-limiting example, a viral particle can be biotinylated by any method that results in the extensive covalent attachment of the biotin molecules to the envelope protein of the virus. Such extensive biotinylation blocks the function of the envelope protein, thereby making the virus non-infectious in the absence of an adapter having a ligand portion complementary to a linking site on the viral particle. In this embodiment the biotin itself provides the linking site. In addition to ecotropic retroviruses, viruses that can be employed to construct vectors according to this embodiment of the invention include amphotropic retrovirus, herpes virus, adenovirus and adeno-associated virus.

The embodiments of the invention are described in greater detail hereinafter.

5.1. The Complex of an Unmodified Virus Particle and an Adapter

In one embodiment the vector complex consists of a vector having one or more envelope proteins that are substantially identical to the virion surface protein or proteins of the parent virus. As used herein, unless otherwise indicated, an envelope protein of a virus is any protein of a viral particle accessible to macromolecules, i.e., an exposed surface protein. A viral envelope protein is an envelope protein which is a non-artifactual constituent of a virus, e.g., the product of the env gene of an ecotropic retrovirus.

The adapter is a molecule, not covalently bonded to the viral vector particle, that has two functionalities. The first functionality consists of a defined number of sites that specifically and stably bind to an envelope protein of the particle. This functionality of the adapter can be a peptide, an oligonucleotide, an antibody or an antigen binding fragment of an antibody, or a polypeptide derived from an envelope binding domain of the natural receptor of the virus or a homolog of a natural receptor. The second functionality consists of a defined number of binding sites that specifically and stably bind to an acceptor molecule that is exposed on the target cells surface. In a preferred embodiment the two functionalities are synthesized as distinct portions of a single polymer. When the functionalities are polypeptides, the adapter is a fusion protein.

An illustrative specific embodiment of the invention is provided in co-pending commonly assigned, U.S. patent application Ser. No. 08/132,990, filed Oct. 7, 1993, which is hereby incorporated by reference. In this embodiment, the envelope binding function is subserved by a fragment of a protein that is the human homolog of the murine ecotropic virus receptor, which has been further modified so that it binds to the ecotropic virus gp70. The target cell binding function is subserved by the antigen binding fragment from the monoclonal antibody B3 that binds to a carbohydrate moiety on a human mucinous carcinoma. Pastan, I., et al., 1991, Cancer Research 51:3781.

5.2. The Complex of a Modified Viral Vector and an Adapter

5.2.1. The Modification of the Envelope Proteins

The modification of the viral vector can be performed either before or after the producer cell line is established. When the modification is performed after the producer cell is established, the producer cell line supernatant is concentrated and the viral particles are then further purified by gel filtration or sucrose density gradient centrifugation, following techniques known to those skilled in the art. After purification the viral particles can be modified by any chemical technique which causes the formation of covalent bonds in proteins without causing their denaturation or causing the disruption of the lipid membrane of the virus in the case of enveloped viruses. In a preferred embodiment the chemical modification is performed by the reaction of a biotin-N-hydroxysuccinimide (biotin-NHS) with the virus. Although this reaction renders the virus non-infectious, absent an adapter, such viral preparations are, nonetheless, suitable for the practice of the present invention.

Other techniques of chemical modification of the viral particles that can be used to practice the invention include the use of photoactivatable reagents, e.g., N-(4'-azido-nitrophenylamino) group linked to biotin (PHOTOBIOTIN), and the use of an activated disulfide, i.e., dithio-2-pyridyl containing compound, to modify the envelope proteins of the viral particles.

In an alternative embodiment the invention can be practiced by modification of a viral envelope protein, a non-limiting example being the env gene of a murine ecotropic retrovirus, prior to the production of viral particles in the producer line. According to this embodiment of the invention a fusion protein is constructed by recombinant DNA technology. The recombinant gene encoding the fusion protein is then transfected into a producer cell line. In one embodiment, the envelope protein of the vector does not bind to the cells of the target cell species, genes encoding both the normal envelope protein and a fusion protein containing a fragment of the envelope protein can be present in the producer line. In the alternative embodiment wherein the complete envelope protein of the vector bind to such cells, the envelope protein gene is replaced by the envelope protein/binding peptide fusion protein gene.

The envelope protein portion of the fusion protein is selected so that the fusion protein is incorporated into the lipid membrane of encapsulated (enveloped) viral particles or into the outer surface of the capsid of encapsidated viruses. The binding polypeptide is selected to bind to a linking molecule, i.e., to provide a "linking site". The stability and suitability of any given candidate fusion protein can be readily determined, once the gene encoding it is constructed. The gene encoding the candidate fusion protein can be transfected into a suitable cell line, e.g., an NIH 3T3 cell, and the expression on the transfected cells' surface of a functional fusion protein can be determined by exposure to a complementary ligand portion of the linking molecule, complexed with a reporter molecule such as a fluorescent tag. In a non-limiting example the binding polypeptide is a fragment of streptavidin encoding residues 16–133 of the streptavidin protein and the remainder of the protein is derived from the env gene of the AKR Virus. Two fragments of a gene encoding a envelope protein are used in the example: a 507 bp fragment extending from the U5 region and including the env protein leader, extending from residue $Met^{-49}$ to residue $Pro^{-1}$ and a 1323 bp fragment that encodes residues $Gly^{223}$ to the carboxy terminal $Glu^{638}$ of the env protein. The sequence numbering of Lenz, J., et al., 1982, J.Virol. 42:519, which is hereby incorporated by reference, is used. The resultant viral vector has a linking site that is complementary to a biotin molecule.

5.2.2. The Linking Molecule

The linking molecule can be any molecule that has functionalities that specifically and stably bind to, firstly, the linking site, provided on the envelope protein of the vector particle and, secondly, to the exposed acceptor on the target cell. The functionalities are termed hereinafter, respectively, the "ligand portion" or "ligand" and the target cell "acceptor binding portion" or "acceptor binder". It is necessary for the invention that the functionalities be different, i.e., that the ligand portion does not form a stable complex with the acceptor nor the does the acceptor binder form a stable complex with the linking site. The complex can be pre-formed most readily when there are defined numbers of both types of functionalities. The number of predefined sites of the acceptor binding functionality is not critical to the invention. The number can be one or more than one. For use in vivo it is preferred that the number of acceptor binding functionalities on each linking molecule be small, most preferably between one and four. The number of the ligand portion functionalities on each a linking molecule is not critical and such number need not be predefined and invariable among the linking molecules.

Non-limiting illustrative examples of linking molecules are as follows:

When the linking site is a biotin binding functionality, the ligand portion can be biotin. The linking molecule can be a biotinylated antibody, a biotinylated cytokine or growth factor or the like. The degree of biotinylation is not critical so long as the acceptor binding function is not inhibited. The number of biotin molecules required to form an effective vector complex is not critical. Variation of the time of the reaction and concentration of the reagents used to biotinylate an acceptor binder can be employed to determine the optimal number of biotins per linking molecule so that the formation of vector complexes occurs in a convenient period of time and at practically attainable concentrations of viral particles.

Alternatively, the linking site introduced into the viral particle can be a biotin. In this embodiment the ligand portion of linking molecule can be comprised of a streptavidin or a streptavidin fragment. When the acceptor binding portion of the linker molecule is comprised of an antibody, the linking molecule can be comprised of a streptavidin/

Protein A fusion protein an example of which is disclosed and claimed in U.S. Pat. No. 5,328,985 and any antibody for a suitable exposed target cell acceptor.

6. EXAMPLES

6.1. Example 1

An Adapter that is Intended to function with an Unmodified Virus

An example of a fusion protein that functions as a soluble adapter for an unmodified ecotropic retrovirus vector is provided by the fusion protein B3(Fv)-Ex3mH13. This fusion protein is based on the B3(Fv)-PE40 fusion protein which is a fusion protein between an antigen binding fragment B3(Fv) and a fragment of an exotoxin. The B3 monoclonal antibody is specific for a carbohydrate antigen present on a mucinous adenocarcinoma and the antigen binding fragment has a similar binding specificity. The PE40 fragment is replaced by the third external domain, residues 210–249 of the human protein H13, which is the human homolog of the murine ecotropic retroviral receptor. In Ex3mH13 the amino acid of the H13 protein at positions 239, 240, 242 and 244 of H13 have been replaced by the amino acid at the homologous position of the murine ecotropic retroviral receptor, so that the Ex3mH13 can be non-covalently affixed to the viral particle by interaction with the gp70 envelope protein of the virus.

The construction of the expression vector, pBH3, which can be used to express the B3(Fv)-Ex3mH13 fusion protein in *E. coli* is described in detail Example XI of co-pending, commonly assigned U.S. patent application Ser. No. 08/132,990, filed Oct. 7, 1993, which is herewith incorporated by reference and in patent publication WO 93/25682 to Meruelo and Yoshimoto, published Dec. 23, 1993. The plasmid pBH3 can be used to express the B3(Fv)-Ex3mH13 fusion protein. The plasmid pTGFA/H13, which can be used to express a fusion protein comprising residues 1–50 of $TGF_{\alpha}$and the above-described Ex3mH13 domain has been deposited in the ATCC on Dec. 22, 1994 as ATCC No. 69728.

6.2. Example 2

An Adapter Comprising a Modified Envelope Protein, a Linking Molecule and an Anti-MHC Antibody

6.2.1. Materials and Methods

Viruses and cell lines. All cells used in the current experiments were obtained from the ATCC except for SupT1, which was generously provided by Dr. J. Sodroski (Dana Farber Cancer Institute, Boston, Mass.), and maintained in our laboratory at NYU Medical Center. Producer cell lines, ψ-2BAG (ATCC NO. CRL 9560) and NIH 3T3, Daudi and SupT1 cells were maintained in either Dulbecco's modified Eagle's medium (DMEM) or RPMI-1640 supplemented with 10% heat-inactivated fetal bovine serum (FBS), and a 1% antibiotic/antifungal solution at a final concentration of 100 IU penicillin and 1% fungizone. The subculture procedure involves removal of medium, treatment with fresh trypsin (0.25%) solution for 2–3 min, rising and removal of the trypsin. The cells are then incubated further until they detach, then fresh medium is added. The cells are aspirated and dispensed into new flasks at a ratio of 1:4 to 1:20. Cells were routinely propagated in culture in a standard humidified incubator at 37° C. in a 5% $CO_2$/95% air atmosphere. Falcon (Becton Dickinson, Lincoln Park, N.J.) plastic tissue culture dishes were obtained from Fisher Scientific (Springfield, N.J.). Viruses were periodically tested for acquisition of inappropriate host range by recombination.

Viral purification and concentration. Vector supernatants from producer cell lines were concentrated using the Millipore Pellicon tangential flow filtration system (Millipore, Bedford, Mass.) with a PLMK000C5 cassette (5 square feet, 300,000 NMWL). A pump was used to exert a low membrane feed pressure of 5 psi. Concentration was achieved within 30 min. After concentration the material was aliquoted in 20 ml samples and kept frozen at −70° C. until further use. For purification, 20 ml of concentrated material was either passed through a Sepharose 4BCL (Pharmacia) column or banded through sucrose gradients. For column purification, the Sepharose 4BCL column is pre-equilibrated with phosphate buffered saline (PBS). After loading the material is eluted with PBS and fractions assayed for O. D. at 260 nm. Peak fractions were checked for virus by Western blot using goat anti-gp70 antibodies and rabbit anti-goat alkaline phosphatase. Sucrose density gradient purification was done as previously described (Bach, R., & Meruelo, D., 1984, J. Exp. Med. 160:270).

Bacterial strains and plasmids. *E. coli* strains HMS171 (Campbell, J. L., et al., 1978, Proc. Natl. Acad. Sci., U.S.A. 75:2276–2280) and DH5a (Sambrook, J., et al., 1989, Molecular Cloning: A Laboratory Manual, 2nd ed. Cold Spring Harbor Laboratory Press, Cold Spring Harbor, N.Y.) were used for cloning. Lysogen BL21(DE3) (Studier, F. W., & Moffat, B. A., 1986, J. Mol. Biol. 189:113–130; Studier, F. W., et al., 1990, Methods Enzymol. 185:60–89) was used for expression. This lysogen carries the cloned T7 RNA polymerase gene in the chromosome under the lacUV5 promoter. pTSA-18F is an expression vector for streptavidin-containing chimeric proteins (Sano, T., & Cantor, C. R., 1991, Biochem. Biophys. Res. Comm. 176:571–577). This plasmid carries the DNA sequence for amino acid residues 16–133 of mature streptavidin, followed by a polylinker region, under the T7 promoter ø10. pR1T11 (Löwenadler, B. et al., 1986, EMBO J. 5:2393–2398) carries the protein A gene (Uhlén, M., et al., 1984, J. Biol. Chem. 259:1695–1702) corresponding to the signal peptide (Region S) and the five IgG-binding domains (Regions E, D, A, B, and C), followed by a polylinker placed in the sequence for the cell wall attachment domain (Region X). pLyS carrying the cloned T7 lysozyme gene was used to reduce the basal level of T7 RNA polymerase activity in the host cells (Studier, F. W., & Moffat, B. A., 1986, J. Mol. Biol. 189:113–130; Studier, F. W., et al., 1990, Methods Enzymol. 185:60–89)

Construction of expression vectors. pTSAPA-2 was kindly provided by Drs. Takeshi Sano and Charles Cantor. The construction and use of pTSAPA-2 can be found in U.S. Pat. No. 5,328,985. Sano and Cantor constructed the pTSAPA-2 vector by inserting a part of the protein A gene into an expression vector for streptavidin-containing chimeric proteins pTSA-18F. pTSAPA-2 was constructed by inserting a 490 bp Rsa I-Hind III fragment of pR1T11 (filled-in using DNA polymerase I large fragment) encoding two IgG-binding domains (Regions E and D) into the Sma I and BamH I (filled-in) sites of pTSA-18F.

Expression of streptavidin-Protein A chimeric proteins. Expression of the gene fusion of streptavidin with protein A was carried out essentially according to the method previously described (Sano, T., & Cantor, C. R. 1990, Proc. Natl. Acad. Sci. U.S.A. 87:142–146; Sano, T., & Cantor, C. R. Biochem. Biophys, Res. Comm. 176:571–577). Lysogen BL21(DE3)(pLysS) was obtained from Novagen. It was transformed with an expression vector and grown at 37° C. with shaking in LB medium supplemented with 1 mM $MgSO_4$, 0.2% glucose, 1.5 $\mu$M thiamine, 0.5% casamino acids (Difco Laboratories), 2 $\mu$g/ml biotin, 150 $\mu$g/ml ampicillin and 34 $\mu$g/ml chloramphenicol. When the absorbance at 595 nm of the culture reached 0.6, 100 mM isopropyl-β-D-thiogalactopyranoside dissolved in water was added to a final concentration of 0.5 mM to induce the T7 RNA polymerase gene placed under the lacUV5 promoter. After the induction, the cells were incubated at 37° C. with shaking. Expression in minimal medium had the advantage that proteolysis of the expressed chimeric protein was substantially reduced.

Purification of streptavidin-protein A chimeric protein. Purification of the expressed streptavidin-protein A chimeric protein was carried out at 4° C. or on ice, unless otherwise stated. The culture (100 ml) of BL21(DE3)(LysS)(pTSAPA-2) incubated for 2 hours after the induction was centrifuged at 2,900×g for 15 min. The cell pellet was suspended in 10 ml of 2 mM EDTA, 30 mM Tris-Cl (pH 8.0), 0.1% Triton X-100, 0.5 mM PMSF to lyse the cells and the lysate was stored frozen at −70° C. until used. To the thawed cell lysate, PMSF, leupeptin, and pepstatin A were added to a final concentrations of 0.5 mM, 1 µM, and 1 µM, respectively. The addition of the proteinase inhibitors reduced degradation of the expressed chimeric protein at early stages of the purification. The lysate was then treated with 10 µg/ml deoxyribonuclease I and 10 µg/ml ribonuclease A in the presence of 12 mM MgSO$_4$ at room temperature (≈20° C.) for 20 min. The mixture was centrifuged at 39,000×g for 15 min, and the precipitate was dissolved in approximately 100 ml of 7 M guanidine hydrochloride. The solution was dialyzed against 150 mM NaCl, 50 mM Tris-Cl (pH 7.5), 0.05% Tween 20, 0.1 mM PMSF, 1 µM leupeptin, 1 µM pepstatin A, 0.02% NaN$_3$. To achieve slow removal of guanidine hydrochloride, the dialysis bag containing the protein solution was left overnight in the dialysis solution (≈1,000 ml) without stirring, followed by several changes of the dialysis solution and dialysis with stirring. The dialysate was centrifuged at 39,000×g for 15 min, and the supernatant was applied to an IgG Sepharose 6 Fast Flow column (1.2×1.1 cm) previously equilibrated with 150 mM NaCl, 50 mM Tris-Cl (pH 7.5), 0.05% Tween 20. Unbound proteins were removed by washing the column with the same solution, and the column was washed with 2.5 ml of 5 mM ammonium acetate (pH 5.0). The bound protein was eluted with 0.5 M acetic acid adjusted pH to 3.4 with ammonium acetate, and dialyzed against 1.0 M NaCl, 50 mM sodium carbonate (pH 11.0). The dialysate was clarified by centrifugation at 39,000×g for 15 min. Each fraction was then tested for activity by ELISA. The activity was found to elute in fractions (1 ml each) one through five, which were pooled and applied to a 2-Iminobiotin agarose (24) column (1.2×1.2 cm) previously equilibrated with the 10 bed volumes of 1M NaCl, 50 mM NaCHO$_3$ (pH 11.0). After unbound proteins were removed with 1M NaCl, 50 mM NaCHO$_3$ (pH 11.0), the bound proteins were eluted with 6M urea, 50 mM ammonium acetate (pH 4.0). The eluted proteins were dialyzed 3 times against Tris-buffered saline (TBS; 150 mM NaCl, 20 mM Tris-Cl (pH 7.5)) containing 0.02% NaN$_3$, and the dialysate was stored at 4° C. after filtration through a 0.22 mm filter (Millex-GV, Millipore). Each fraction was again tested for activity by ELISA.

Viral infectivity assays and titering. On day 1 NIH3T3 cells were seeded at 1×10$^5$ cells/well of a six-well tissue culture plate (Becton Dickinson, Lincoln Park, N.J.) and incubated at 37° C. in 5% CO$_2$. On day 2, serial ten-fold dilutions of vector specimen in medium containing 8 µg/ml Polybrene were added to the target cells and incubated at 37° C. for an additional 4 hr, after which the medium was removed and replaced with regular medium containing 2 µg/ml Polybrene. Cells were assayed for X-gal activity 48 hr later. Vector titer was calculated as the number of colony forming units (cfu) per ml. For 5-bromo-4-chloro-3-indolyl-β-D-galactosidase (Sigma) (X-gal) visualization of β-galactosidase (β-gal) activity in intact cells, the method of Dannenberg and Suga (Methods for Studying Mononuclear Phagocytes, Ed. by Adams, D. O., et al., (Academic Press, New York), pp. 375–396, 1981) was used, following fixation in 0.5% glutaraldehyde for 15 min.

Determination of concentration of proteins. To determine protein concentrations we used the standard and micro assay procedures recommended by the Bio-Rad. For the standard procedure, we prepared several dilutions of protein standard (supplied) containing from 0.2 to about 1.4 mg/ml. We then placed 0.1 ml of standard and appropriately diluted samples in clean, dry test tubes. We placed 0.1 ml sample buffer in "blank" test tube. We added 5.0 ml of diluted dye reagent (provided), vortex, and after 5 minutes to one hour, measured the OD$_{595}$ versus the reagent blank. These OD$_{595}$ values were plotted versus concentration of standards and the unknown values were determined from the standard curve. For the microassay procedure, protein standard from 1 to 25 µg/ml were used, and 0.8 ml of appropriately diluted samples were used with 0.2 ml of dye reagent concentrate. Both procedures are otherwise the same.

Biotinylation of viruses. Biotin-N-Hydroxysuccinimide ester (biotin-NHS) (biotin-X-NHS, Calbiochem, Catalog No. 203187) was used to biotinylate the envelope proteins. Biotin-X-NHS introduces a spacer between the biotin and target ligand, reducing steric hindrance that can diminish the efficiency of streptavidin binding. For this procedure, 1 mg of virus were dissolved in 0.9 ml of sterile distilled water. A 0.1 ml of a 10×Buffer (NaHCO$_3$) was added and vortexed. Freshly prepared biotin was used (11 mg Biotin-X-NHS ester in 0.25 ml dimethylformamide) at a 0.1 M concentration. This biotin solution was added to the equilibrated protein solution and incubated at room temperature for one hour with gentle agitation using a rocker. At the end of the hour the protein-biotin solution was dialyzed several times against 0.01 M PBS, pH 7.3, to remove unreacted biotin-X-NHS ester. The biotin-labeled protein solution was stored at 4° C. until further use.

FluoReporter lacZ Flow cytometry. We chose to use a fluoreporter "lacZ" flow cytometry assay for the detection of lacZ-β-Galactosidase in single cells developed from Molecular Probes, Inc. (Eugene, Oreg.).

Chromogenic β-galactosidase substrates such as o-nitrophenyl-β-D-galactopyranoside (ONPG) and 5-bromo-4-chloro-3-indolyl galactoside (X-gal) have been widely used to monitor β-galactosidase activity resulting from lacZ gene expression. However, chromogenic lacZ assays are relatively insensitive and require the use of bulk cell extracts. More recently, measurements of the fluorescence resulting from enzymatic cleavage of fluorescein di-β-D-galactopyranoside (FDG) has been utilized to develop a lacZ assay based on fluorescence-activated cell sorting analysis which is at least eight orders of magnitude more sensitive than chromogenic methods. Another benefit of the method is that it permits analysis of individual cells in a population by use of the FACS analyzer.

All reagents were obtained from the manufacturer and used as recommended by the manufacturer. Essentially, in this method a cell suspension is prepared from exponentially growing cells and the substrate FDG is loaded into the cells at 37° C. by hypotonic shock. The loading process is terminated by dilution of the cells into ice-cold isotonic media. At this low temperature, the cell membrane is relatively impermeable to the substrate and hydrolysis results. With the substrate and products locked inside each cell, the rate of hydrolysis of the substrate to fluorescein is monotonicly related to the concentration of β-galactosidase in each individual cell. The reaction can be stopped by addition of a competitive inhibitor, phenylethyl-β-D-thiogalactopyranoside (PETG), making the timing of the reactions more convenient. Propidium iodide staining is used to detect cells which have been lysed (dead cells). The inhibitor, chloroquine, is available to lower lysosomal pH level and prevent nonspecific lysosomal hydrolysis.

FACS analysis. Cells are resuspended in 10 ml of PBS with 1% BSA and in some cases 0.1% sodium azide. Cell counts are done and viabilities recorded. Cell concentrations are adjusted to $1\times10^6$/ml. A 1 ml aliquot is placed in each tube and cells are spun-down. Cells are then incubated with the appropriate dilution of antibodies in 50 μl at 4° C. or at room temperature for 30 min. Cells are then spun and washed 2× with 1 ml of PBS with 1% BSA and 0.1% sodium azide. The pellet of the last wash is then incubated with an secondary reagent if appropriate, and incubated further at 4° C. or at room temperature for 30 min. Cells are then spun and washed 2× with 1 ml of PBS with 1% BSA and 0.1% sodium azide. After the last wash the cells are resuspended in 300 μl of PBS with 1% BSA and 0.1% sodium azide and 300 μl of 2% paraformaldehyde, to fix them, prior to FACS analysis in an FACScan, Becton Dickinson, Lincoln Park, N.J.

Preparation of the Complex and Transduction of Non-adherent Cells. The viral vector complex was prepared by mixing about 10 μl each of biotinylated viral particles, antibody and SA-PA fusion protein, each having approximately 0.3 mg/ml of protein, in a microcentrifuge tube. The mixture was incubated for 10 minutes at 22° C. Thereafter, $2\times10^6$ cells were suspended in 1 ml of fresh complete medium and incubated four hours at 37° C. in a $CO_2$ incubator. Thereafter, the cells were fed with an additional 4 mls of medium and cultured until FACS analysis at 48 hours post transduction.

6.2.2. Transduction of Ex Vivo Target Cells with βgal

To detect infection by ecotropic viruses, we used a 48 hour assay involving the lacZ gene which encodes a β-galactosidase. No selection process was required in this assay and good quantitation can be achieved by the fluoreporter lacZ flow cytometry assay for the detection of lacZ encoded β-galactosidase in single cells (Fiering, S. N., et al., 1991, Cytometry 12:291–301; Nolan, G. P., et al., 1988, Proc. Natl. Acad. Sci. U.S.A. 85:2603–2607; Molecular Probes, Inc.).

In this assay, only cells with fluorescence greater than a predetermined level are considered infected. The predetermined level varied from cell to cell type. A small number of cells in the uninfected population were above the selected fluorescence level and these represented the background level of the assay.

ψ-2BAG, a murine ecotropic virus, was unable to infect a human B lymphoblastoid cell line, Daudi. However, when this virus was biotinylated and used in conjunction with the Streptavidin/ Protein A (SA-PA) fusion protein and either of two mAbs specific for exposed acceptors on these cells (anti-HLA-DR and anti-CALLA mAbs), infection of Daudi cells is readily achieved, as is shown below.

TABLE I

Transduction of Daudi Cells

| ψ-2BAG | SA-PA | Antibody | % β gal staining |
|---|---|---|---|
| No | No | None | 2.8 |
| Yes | No | None | 4.8 |
| Yes | Yes | anti-HLA-DR | 31.6 |
| Yes | Yes | anti-CALLA | 24.4 |
| Yes | Yes | anti-CD4 | 5.2 |

Daudi cells were not transduced when a mAb (anti-CD4) was used that did not bind to Daudi cells. Since Daudi cells are not transduced by ψ-2BAG, these results demonstrate that the use of a vector complex comprising a murine ecotropic virus having a lacZ gene as the gene of interest, and an adapter comprising biotin, a SA-PA fusion protein and mAbs specific for a target cell receptor was operable. It showed infection of specific human cells, by murine ecotropic retroviruses.

A variety of cell lines were tested using biotinylated ψ-2BAG, targeted by specific mAbs and the SA-PA fusion protein are shown in Table II, below. Of four cell lines tested SupT showed the highest rate of infection. These data demonstrated that the invention can be successfully used for various cell lines. Thus JURKAT cells was infected by the FP-based approach, whether CD4 or CD3 molecules were targeted and CCL119 was infected by targeting CD4, CD3, or CD10.

FIG. 1 is a histogram of the fluorescence intensity of SupT without transduction and after transduction with the above-described viral vector complex.

TABLE II

Transduction of Various Cell Types

| Cell line | Antibody | % R* | % Cont.+ |
|---|---|---|---|
| KG-1 | CD34 | 1.8 | 0.9 |
| Molt-4 | CD4 | 22.4 | 1.2 |
| Jurkat | CD3 | 6.8 | 1.5 |
| Jurkat | CD4 | 4.4 | 1.5 |
| CCL119 | CD3 | 5.9 | 1.8 |
| CCL119 | CD4 | 5 | 1.8 |
| CCL119 | CD10 | 10 | 1.8 |
| SupT1 | CD4 | 95 | 7.8 |
| SupT1 | CD4 | 93** | 7.8 |

*The percent of transduced cells with β-galactosidase dependent staining greater than threshold.

6.2.3. Transduction of In Vivo Targets by Vector Complexes

To demonstrate the operability of the invention in vivo nude mice were injected with human Daudi cells, and the tumor cells allowed to grow for about 4 weeks. At this point mice were injected intraperitoneally and intratumorally with a vector complex comprising a β-gal containing biotinylated ecotropic retroviral particle, linked to a anti-HLA-DR-PASA. Two days later the tumor cells were removed and examined by double fluorescence for β-galactosidase activity and presence of HLA-DR determinants. Although, in theory, the ecotropic virus might have been infectious for the host (murine) cells, previous experiments had shown that the biotinylated viral particles were non-infectious in the absence of an adapter. The results of this experiment were that 77.3% of the recovered cells were HLA-DR positive, 10.2% β-galactosidase positive, and 8.6% positive for both β-gal and HLA-DR. Thus, the bulk of β-gal positive cells were HLA-DR positive (83%).

The interpretation of the following experiment depends upon the inability of the biotinylated vectors, without adapters, to infect murine cells. CD4 murine cells were targeted by the intravenous administration into mice of a viral complex having an adapter consisting of a biotin on an envelope protein of the ecotropic viral particle, various concentrations. Control mice were infected only with individual components of the complex. Several days after injection of the fusion protein, animals were sacrificed and assayed for fluorescence intensity in the T and B cell populations of various organs (i.e., thymus, spleen and mesenteric lymph nodes). A comparative enrichment of the β-galactosidase activity was seen in CD4 populations in organs of mice receiving the anti-CD4-FP-V complex. Representative results are shown in FIG. 2. In this figure the mean fluorescence intensity of the double positive population (CD4/β-gal) ranged from 138.22 to 163.94 in organs taken from control mice. However, mean fluorescence intensity for CD4/β-gal positive cells increased to anywhere from 326.50 to 452.17 for lymphocytes taken from animals receiving the complete vector complex. By contrast non-targeted B (B220 positive) cells did not demonstrate an increase in β-gal mean fluorescence intensity in any of the animals. Double positive B220/β-gal demonstrated a mean fluorescence intensity ranging from 117.31 to 138.96 in control mice and between 131 and 137.04 in animals receiving the complex.

6.2.4. A Linking Molecule with Non-Antibody Acceptor Binder

The adapter comprising a fragment of containing residues 16–133 of streptavidin, and residues 1–50 of TAGα was constructed. The fusion protein is expressed by the methods as described hereinabove concerning the SA-PA fusion protein. The plasmid PTSALA, which can used to express the TAGα-SA fusion protein, has been deposited on Dec. 22, 1994 as ATCC No. 69729.

6.3. Selection of the Acceptor on the Target Cell

In the preferred embodiment of the invention, the binding of the vector complex to the acceptor molecule on the target cell will be followed directly by the internalization of the complex. The suitability of a particular differentiation antigen can be determined by observing the rate of internalization of the of the complex. The rate of internalization can be determined by staining with a fluorescence-labeled antibody specific for an element of the adapter, typically an anti-immunoglobulin antibody. The time course of internalization of a complex of biotinylated viral particles, SA-PA fusion proteins and a monoclonal antibody was observed for complexes comprising anti-CD4 on SupT1 cells and anti-HLA-DR on Daudi cells. The results are shown in FIG. 3.

We also examined the relationship between the fusogenic activity of the virus and transduction by the vector complex. Dextran sulfate has been shown to inhibit viral-mediated fusion. Dextran sulfate (DS) inhibited the transduction of Daudi cells with β-gal mediated by an anti-HLA-DR monoclonal antibody containing vector complex: Control 21% β-gal positive; 2 μg DS/ml, 10% positive; 6 μg DS/ml, 6% positive. This observation leads one to conclude that the fusogenic activity of the virus plays an important part of the mechanism of entry of retrovirions mediated by FP complexes.

6.4. An Adapter that Comprises an Envelope/Streptavidin Fusion Protein 6.4.1. Construction of the pST-env Plasmid The plasmid pST-env was constructed as follows. Total AKV RNA was isolated from NIH3T3 cell line infected with a clonal isolate of ecotropic AKV murine retrovirus; total viral RNA consisted of a transcript that contained the entire genome and of a spliced transcript that contained only the env gene. The transcripts were reverse transcribed using Superscript RNase H-reverse transcriptase (Life Technologies, Inc., Gaithersburg, Md.) and random hexamer primers (New England Biolabs, Beverly Mass.). Based on published genomic sequences of murine retrovirus AKV, primers were designed to the unique 5' region (FP1: 5'-GG ACTAGT TCC GAA TCG TGG TCT CGC TGA-3' SEQ ID NO: 1) and the carboxyl terminus of the signal peptide of the env gene (RP1: 5'-GGG AAT TC CATATG GGG GTT GAC CCC TCC GAG-3' SEQ ID NO:2). Restriction enzyme sequences for SpeI and NdeI which were engineered into the primers FP1 and RP1, respectively, are in italics and irregularly grouped.

A 507 bp portion of the env gene (containing the U5 and the signal peptide of envelope protein) was amplified by PCR (Perkin-Cetus Corpn., Norwalk, Conn.) using FP1 and RP1 as the primers. This amplified fragment was cloned directly into the TA cloning vector PCR II (Invitrogen Corp., San Diego, Calif.) between the two EcoRI sites, and checked by restriction enzyme digestion and sequence. The vector PCR II with the correct insert was digested with NdeI and KpnI, creating a NdeI-KpnI fragment of approximately 4.4 Kb length. The plasmid pTSAPA-2 (obtained as in section 6.2.1 containing an insert encoding a streptavidin-protein-A chimeric protein was digested with the enzymes NdeI and KpnI. A resulting 360 bp fragment containing the truncated streptavidin was legated into the cut vector PCR E which contained the U5+ leader peptide. One clone, PCRII-10b4ST, which has the 862 bp of correct insert was obtained and digested with SpeI and EcoRI to release the fragment of interest.

The AKV env gene (cloned into the SmaI site of the vector pBKCMV) (Lenz, S. et al., 1982, J. Virol. 49:471–8) was digested with BamI-H and HindIII. This gives a 1322 bp fragment which encodes the proline rich region of the AKV gp70 and includes the complete p15E. The BamHI-HindIII fragment was ligated with the SpeI-EcoRI fragment with the aid of linkers EB1 (5'-AAT TCG GGA GGC GGT GGA TCA GGT GGA GGC GGT TCA GG-3 SEQ ID NO: 3)' and EB2 (5' -GAT CCC TGA ACC GCC TCC ACC TGA TCC ACC GCC TCC CG-3' SEQ ID NO: 4) which were compatible with the ends.

The insert encoding streptavidin and the BamHI-HindIII fragment of AKV env was cloned into pCEP4 eukaryotic expression vectors which has a hygromycin resistance gene, and chimeric envelope construct pST-env was obtained. A schematic representation of which is presented in FIG. 4.

Streptavidin containing fusion proteins, which have either the NspI-HindII fragment of the AKV env gene (nts 539–2191), encoding variable region A (vrA) of the gp70 and a p15E or the Esp3I-KpnI fragment of the env gene (nts. 871–2191) that encodes only p15E have been made. These fusion proteins are expressed in packaging cell lines and the portion of the fusion protein derived from env is sufficient to operable to direct the assembly of the fusion protein into the viral particles made by the transfected packaging cell line. The plasmid pST-env was deposited on Dec. 22, 1994 as ATCC No. 69730.

6.4.2. Transfection of a Packaging Cell Line pST-env was transfected to ψ-2BAGα ecotropic-MLV packaging cell line by $CaPO_4$ and lipofectin methods. First, streptavidin expression on the cell surface was examined by using biotinylated IgG and $^{125}$I-Protein A 3 days after transfection. pST-env transfected ψ-2BAGα cells showed higher biotin binding activity than AKV env transfected control. Several transfected clones were picked up after hygromycin selection and examined for its streptavidin expression by FACS analysis by using FITC-biotin X. Some clones showed monophasic shift in fluorescence indicating the expression of streptavidin on the cell surface.

Figure 5A:
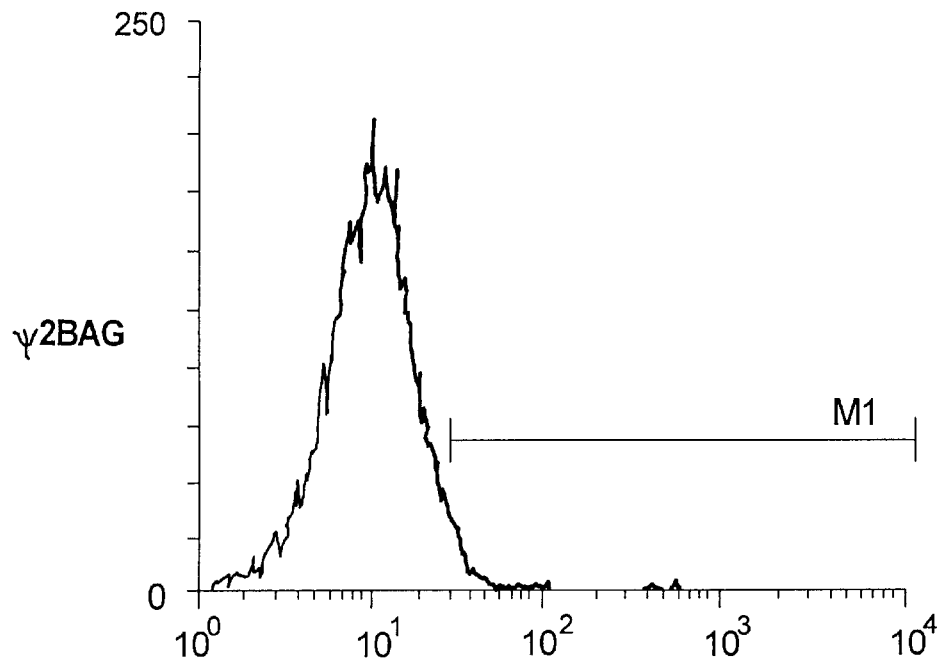
Figure 5B:
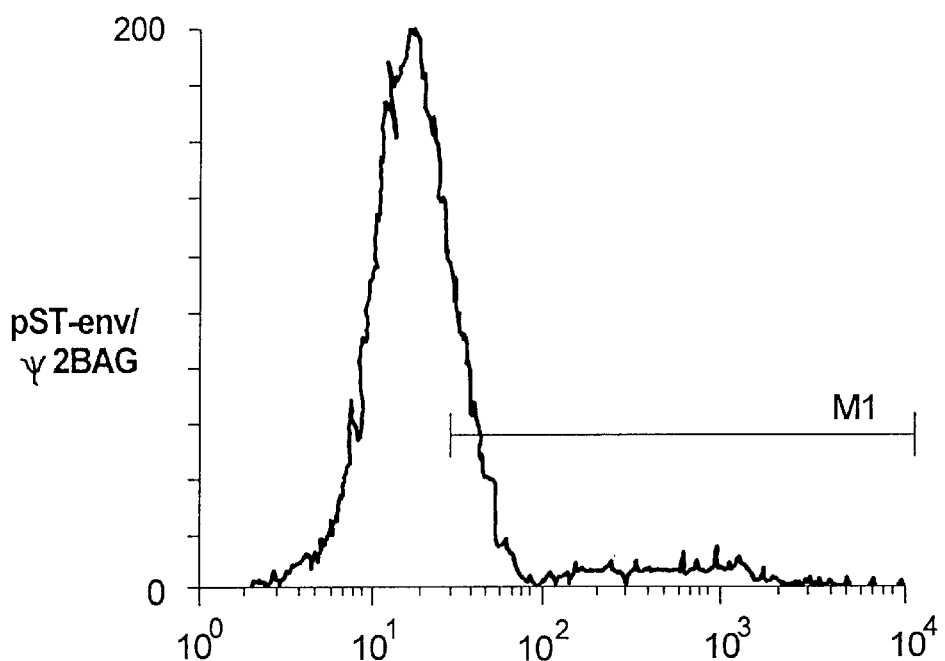

Virus-containing supernatants were harvested from subclones, that were grown to confluence after overnight incubation in serum-free nonselective medium. Virus supernatants were incubated with biotinylated anti-HLA-DR mAb for 30 min at RT then added to Burkitt's lymphoma Daudi cells and incubated for 4 hr at 37° C. Infected cells were examined by lacz-staining flow cytometry (Molecular Probe, Inc.) 3 days after infection. Negative control infections were done with virus similarly harvested from ψ-2BAGα cells. As shown by the comparison of FIGS. 5A and 5B, 20% of Daudi cells transduced with a pST-env-transfected cell line supernatant contained β-gal related staining; control Daudi cells transduced with unmodified ψ-2BAGα supernatants had a level of only 2.7% ψ-gal related staining. This result demonstrated the production of an ecotropic-MLV which contains streptavidin-env fusion protein adapter.

The present invention is not to be limited in scope by the specific embodiments described which were intended as single illustrations of individual aspects of the invention, and functionally equivalent methods and components were within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. A viral vector complex for transducing a target cell with a gene of interest under physiological conditions, comprising:

a. a viral particle, comprising 1. a gene of interest operably linked to a promoter that is active in a target cell;
2. an envelope protein;
3. a biotin molecule covalently affixed to said envelope protein; and b. a bifunctional adapter affixed to said envelope protein, the bifunctional adapter comprising a binding site for a native acceptor on the target cell and a linking molecule comprising a biotin binding site and a binding site for the native acceptor, wherein the linking molecule is non-covalently bonded to said envelope protein.

2. The viral vector complex of claim 1 wherein the binding site for the native acceptor is a binding site for a carbohydrate.

3. The viral vector complex of claim 1 which the acceptor binding site is a fragment of a soluble cytokine selected from the group consisting of erythropoietin, interleukins, interferons, fibroblast growth factors, transforming growth factors, tumor necrosis factors, colony stimulating factors and epidermal growth factor.

4. The viral vector complex of claim 1 in which the linking molecule comprises a Protein A/Streptavidin fusion protein and an antibody molecule that binds to the native acceptor.

5. The viral vector complex of claim 4 in which the native acceptor is selected from the group consisting of class I MHC antigens, class II MHC antigens, internalizing cell-surface receptors and viral receptors and the binding site for a native acceptor is a binding site for a protein portion of the native acceptor.

6. A method of expressing a gene of interest in a target cell which comprises directly contacting the target cell with the viral vector complex of claim 1 under physiological conditions wherein the viral particle is internalized into the cell so that the cell is transduced and expresses the gene of interest.

7. The method of claim 6 wherein the target cell is a target cell cultured ex vivo.

8. The method of claim 6 wherein the target cell is a target cell present in a mammalian animal.

9. A method for preparing a viral vector complex for transducing a target cell with a gene of interest under physiological conditions, comprising:

(a) contacting under conditions suitable for non-covalent bond formation:

(i) a viral particle having a gene of interest operably linked to a promoter which is active in the target cell, and an envelope protein, wherein a biotin molecule is covalently affixed to said envelope protein, with (ii) a bifunctional adapter molecule comprising a binding site for a native acceptor of the target cell and a linking molecule that is capable of non-covalent bonding to said viral envelope protein wherein the linking molecule comprises a biotin binding site and a binding site of the native acceptor, and bonded to the viral envelope protein.

10. The method of claims 9 wherein the envelope protein is a viral envelope protein.

* * * * *